United States Patent [19]

Anada

[11] 4,197,911
[45] Apr. 15, 1980

[54] PROCESS FOR IN SITU COAL GASIFICATION

[75] Inventor: Harish R. Anada, Vienna, Va.

[73] Assignee: Ramcor, Inc., Vienna, Va.

[21] Appl. No.: 904,445

[22] Filed: May 9, 1978

[51] Int. Cl.² .......................................... E21B 43/24
[52] U.S. Cl. ............................. 166/261; 48/DIG. 6;
 166/266; 166/272; 166/302; 166/303
[58] Field of Search ............... 166/256, 259, 261, 272,
 166/299, 302, 303; 48/DIG. 6, 202; 299/2

[56] References Cited

U.S. PATENT DOCUMENTS

| 2,788,956 | 4/1957 | Pevere et al. ............... 48/DIG. 6 X |
| 3,219,108 | 11/1965 | Monroe ........................... 166/261 X |
| 3,225,827 | 12/1965 | Prats ..................................... 166/256 |
| 3,339,634 | 9/1967 | Meter, Jr. et al. ................... 166/261 |
| 3,628,929 | 12/1971 | Glass et al. ..................... 166/256 X |
| 3,770,398 | 11/1973 | Abraham et al. ................ 166/256 X |
| 3,794,116 | 2/1974 | Higgins ................................ 166/259 |
| 3,850,477 | 11/1974 | Aldrich et al. ......................... 299/5 |
| 3,948,320 | 4/1976 | Terry .................................... 166/272 |
| 3,973,628 | 8/1976 | Colgate ............................... 299/5 X |
| 3,990,513 | 11/1976 | Perch ....................................... 299/4 |

*Primary Examiner*—James A. Leppink
*Assistant Examiner*—George A. Suchfield
*Attorney, Agent, or Firm*—James J. Brown

[57] ABSTRACT

In situ coal gasification to form a methane rich gas is carried out by injecting a lower aliphatic alcohol such as methanol into a coal seam, raising the temperature to cause dissociation of the alcohol and injecting water into the same. Nascent hydrogen is produced which reacts with the coal to form methane. The product gas may also contain hydrogen and carbon monoxide which can be separated and reacted to form methanol.

10 Claims, 3 Drawing Figures

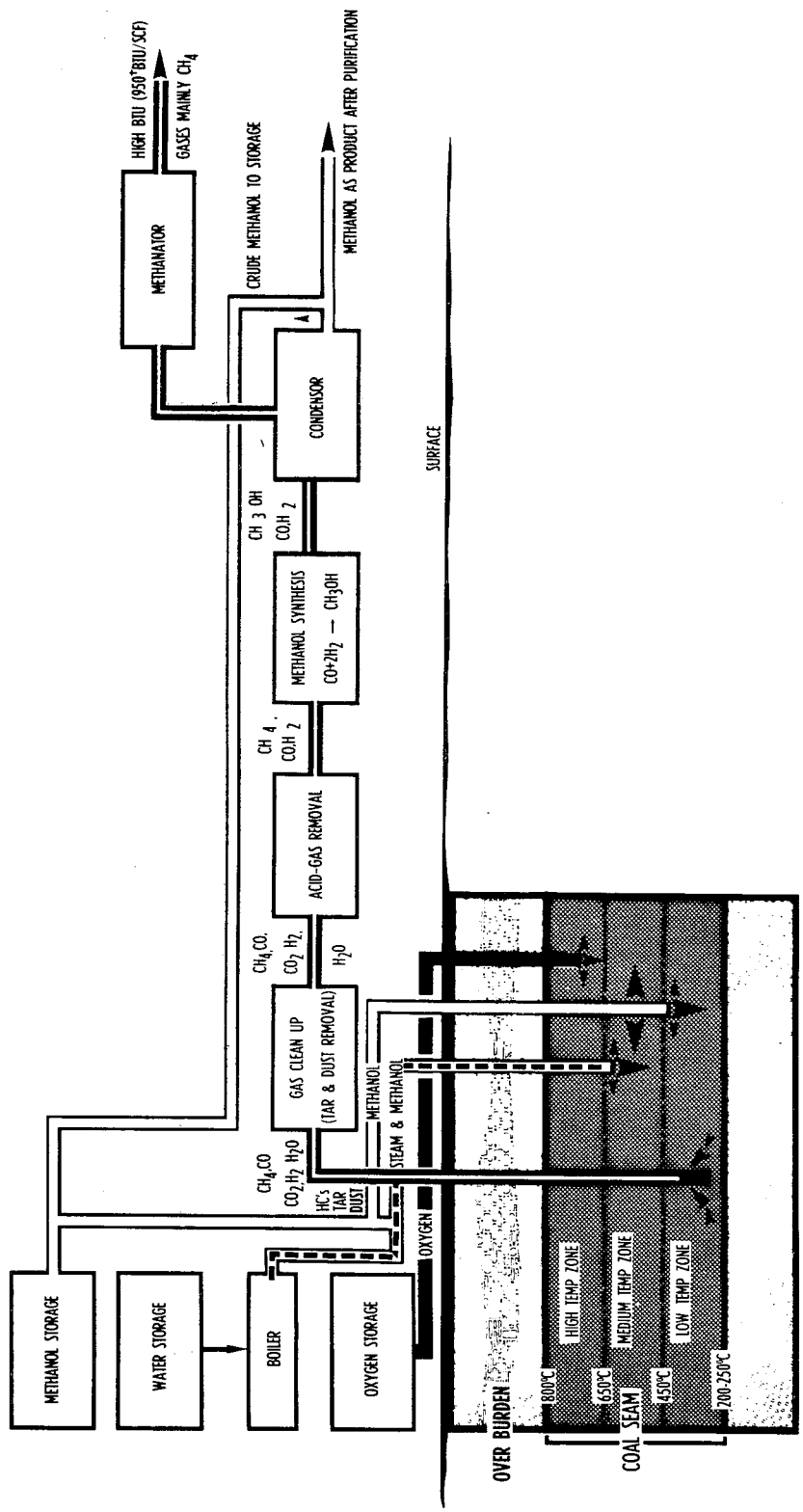
FIGURE 1 SCHEMATIC FLOW DIAGRAM FOR METHANOL-STEAM PROCESS

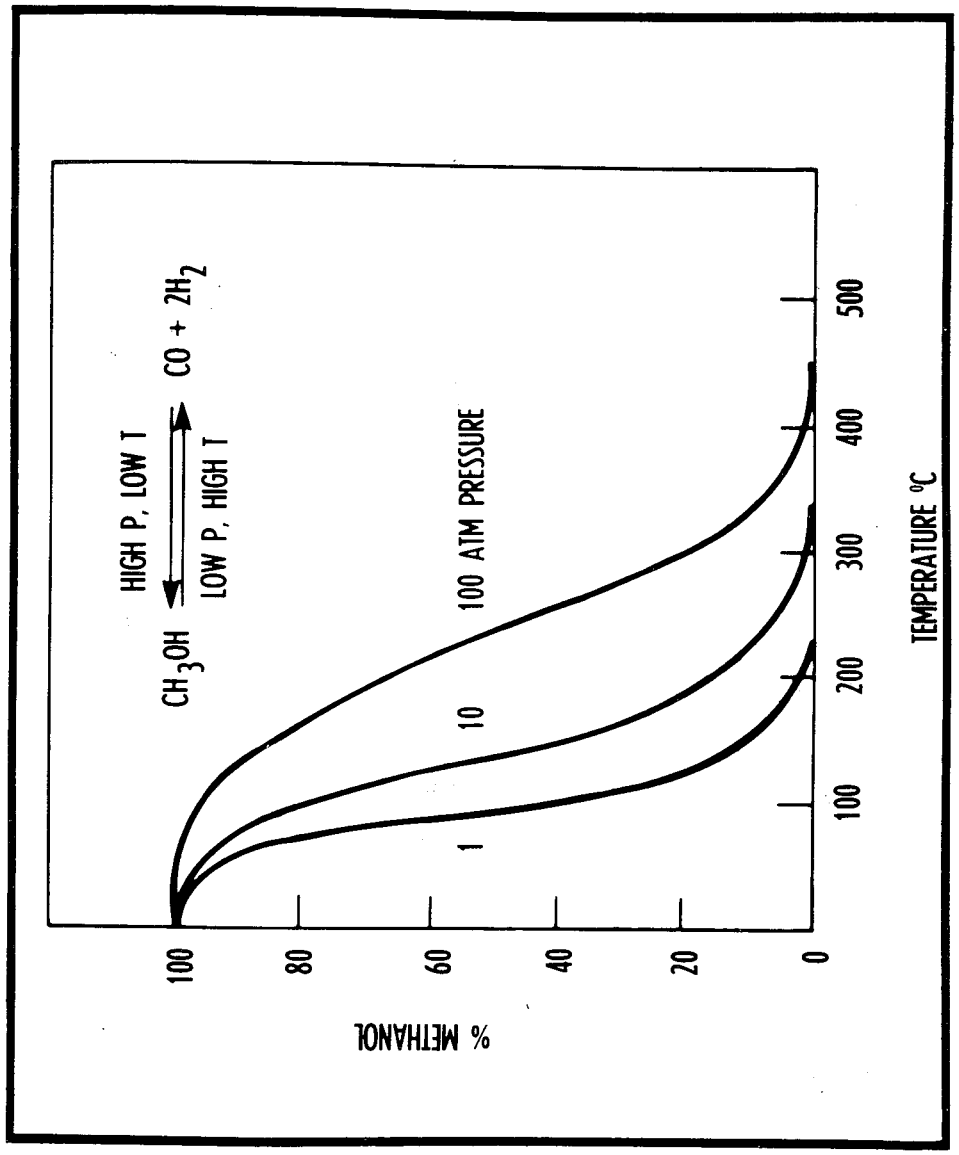
FIGURE 2 METHANOL DISSOCIATION EQUILIBRIA

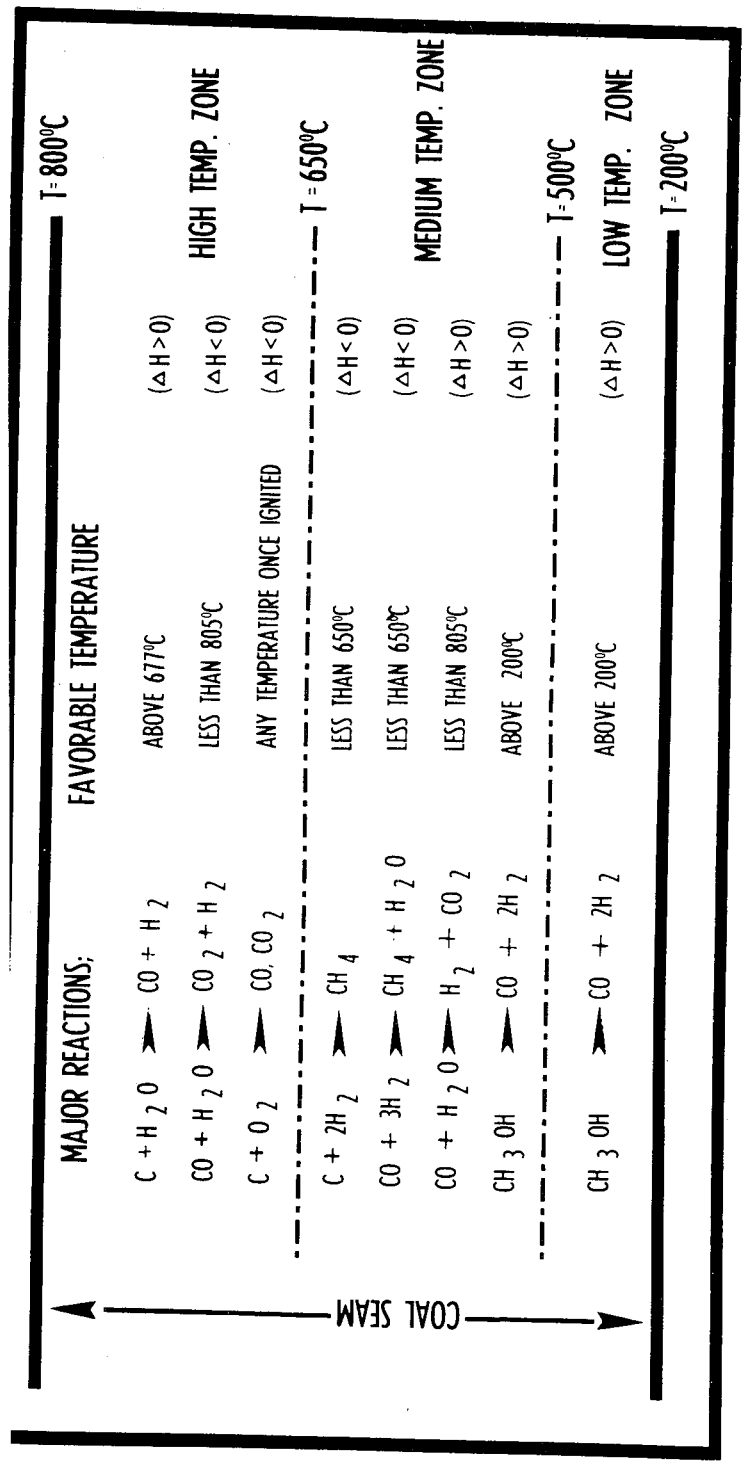
FIGURE 3 REACTION PROFILE IN THE COAL SEAM

PROCESS FOR IN SITU COAL GASIFICATION

The present invention relates to a process for in situ gasification of coal to obtain high BTU gases. More particularly this invention relates to a process involving the injection of methanol and steam into a coal bed to react with the coal to produce methane and other gases. The product gas consists of methane, hydrogen, carbon monoxide, carbon dioxide and steam which can be upgraded to pipeline gas.

BACKGROUND OF THE INVENTION

Coal gasification has become a subject of many studies in recent years as a conversion technique which shows promise of providing a substitute for high BTU natural gas as reserves of petroleum and natural gas diminish. The cost of this substitute natural gas, better known as synthetic natural gas (SNG), may be several times the cost of natural gas which has existed in the past. The major cost of surface coal gasification consists of coal mining cost and cost of the gasification plant. Mining cost increases dramatically when the ratio of the overburden to coal seam thickness increases as in the case of strip mining and as one goes deeper to mine coal by conventional deep mining methods. Also, various environmental and health related problems occur such as surface disruption, health and safety of miners, sulfur removal, pollution from fly ash, waste disposal and others.

Compared to conventional mining of coal combined with surface gasification, underground coal gasification offers a number of significant potential advantages such as:

It can be applied to large reserves not economically recoverable by conventional mining methods;

It minimizes, health and safety problems associated with conventional coal extraction techniques since no mining is required;

It can produce less surface disruption and brings less solid waste to the surface;

It consumes less water and generates less atmospheric pollution;

It reduces socioeconomic impact;

It reduces capital investment and gas cost.

The possibility of underground gasification of slack and waste coal in mines was first suggested by William Siemens in 1868 (Siemens W., Transactions of Chemical Society, 21, 279, 1868). In 1888, Mendeleev in Russia suggested the true underground gasification of coal. In 1909, A British Patent (G.G. 21674) was granted to Ansen Betts who proposed a method of gasifying coal in the bed by igniting the base of one or more shafts or boreholes, supplying it with air and steam and withdrawing the gas formed through either the same or other shafts or boreholes. Small-scale experiments on underground gasification were conducted in England by Sir William Ramsey prior to the first World War. The Russian work, inspired in part by Lenin's recommendations, was of the largest duration, beginning (on a large scale) in about 1933 and extending to about 1965. It reached the state where the extracted gas was used for large-scale generation of electricity and to supply local industries (see Report No. UCRL-52004 and SAND 76-0380 available from NTIS, Springfield, Va.). Outside Russia most of the activity occurred in the post World War II period from about 1945 to 1960. At one time during this period, simultaneous large-scale experimental work was underway in England, France, Belgium, the United States, Italy and continuing work in USSR; and probably in Poland, Czechoslovakia and Japan. (See Chapter 21, Chemistry of Coal Utilization; Supplementary Volume, by H. H. Lowry, John Willey & Sons, New York). Some of the operations were claimed to be promising but availability of lower cost petroleum and natural gas prevented further development. In all cases, work appears to have ceased mainly for lack of economic incentives, until recently when shortage of petroleum and natural gas became prominent and the price of oil and natural gas escalated significantly. Renewed interest in the last few years has again stimulated research in underground coal gasification area.

Underground coal gasification involves two basic steps: (1) preparation of the coal seam and (2) gasification of the coal. The majority of the emphasis is being placed on the first step, i.e., to prepare the coal seam to improve the permeability of coal by development of a variety of fracturing methods, novel drilling techniques and by development of the configuration of boreholes, etc.

Very little emphasis has been placed on the second step, i.e., in gasification process tactics inside the coal seam. Most of the processes of the prior art have been based on air injection or air and steam injection where the product gas Btu content is very low. However, little attention has been given to the chemistry of coal gasification inside the coal seam and on improvement of the heat content of the product gas. U.S. Pat. No. 3,734,184 to Scott has suggested a method for distilling coal in situ by treating a rubblized bed of coal with super heated steam to recover hydrocarbons and to improve the Btu content of the product. U.S. Pat. No. 3,794,116 to Higgins has suggested use of oxygen and steam instead of air to improve the Btu content of the product gas.

OBJECTS OF THE INVENTION

It is accordingly one object of the present invention to provide a new method for the gasification of underground coal beds which provides an improved quality of product gas compared with existing underground gasification processes.

A further object of the invention is to provide a method by which the in situ gasification of coal can be carried out to provide increased conversion of the coal by taking advantage of the unique properties of methanol to improve the permeability of the coal.

A still further object of the present invention is to provide a method which encourages a methanation reaction in the coal seam.

It is still a further object of the invention to provide a method which reduces the overall temperature requirements for gasification of the coal seam as compared with prior art techniques thus reducing the heat loss to the surrounding strata.

SUMMARY OF THE INVENTION

The present invention is directed to a process for gasifying coal in situ by injecting methanol and steam into the coal seam and raising the temperature in the seam sufficiently to vaporize the methanol and cause its dissociation, which provides highly reactive form of hydrogen (nascent hydrogen) for hydrogasification reactions which produce a methane-rich product gas of high BTU value. To assist the initial permeation of the methanol into the coal seam it may be desirable to first fracture the seam using conventional techniques involving drilling and explosive fracturing. Conventional techniques such as drilling boreholes are utilized for providing access holes to the seam for the reactants. The product gas obtained by the invention can be piped out of the seam using conventional techniques and purified, separated and stored as desired.

BRIEF DESCRIPTION OF THE DRAWINGS

FIG. 1 is a schematic representation of the process of the present invention.

FIG. 2 is a graph showing extend of methanol dissociation into carbon monoxide and hydrogen at various temperatures as a function of pressure.

FIG. 3 is a summary of various reactions occurring in the coal seams at different temperatures.

DETAILED DESCRIPTION OF THE INVENTION

As shown in FIG. 1 of the drawings, the basic feature of the process of the present invention is the utilization of a lower aliphatic alcohol such as, preferably, methanol ($CH_3OH$) or ethanol ($CH_3CH_2OH$) along with steam to supply a highly reactive form of hydrogen for gasification of coal. Oxygen air or other means may be used in small quantities to increase the temperature which initiates the reactions, however, once the process starts and reaches an optimum level, there is no need to supply oxygen because the heat requirement for endothermic reactions is supplied by exothermic reactions (see Table 1).

According to the present invention, following any necessary preparation of the coal seam alcohol is injected into the coal seam. Methanol ($CH_3OH$), especially, has the unique property of being absorbed by coal thoroughly. The absorption of a methanol molecule in coal is not completely understood, but the characteristics are unique and yield surface areas approaching 200 cu. m./g. compared to nitrogen values of only 1 cu. m./g. One possible explanation is that the methanol molecule is very small and fits within a cube 4 A° to a side. It can easily penetrate in the cracks and pores within coal which have been estimated to be about 40 A° wide and are interconnected by constrictions of 5–8 A° width. This unique adsorption of methanol insures that an excellent and intimate distribution of hydrogen source is obtained within a coal particle.

Following injection of the methanol, temperature in the coal seam is then increased by suitable procedures such as injecting a small amount of oxygen and starting combustion near the top of the broken zone with a methane flame. Using these procedures the upper portion of the coal seam is ignited and oxidation of carbon in the coal increases the temperature of the coal seam. The optimum temperature in the seam is 750° to 800° C. at top and about 250° C. at the bottom of the seam and pressure in the seam can be about 10 atm. to 50 atm.

When the temperature of coal seam increases, the temperature of methanol in the coal seam also increases. At about 62.4° C. methanol starts to convert into vapor which easily penetrates through cracks and pores of the coal. Further increases in temperature initiates the decomposition of methanol according to the following reactions:

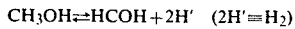

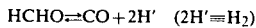

overall reaction
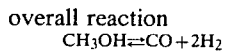

The decomposition of methanol is a free radical reaction which yields four moles of nascent hydrogen. This highly reactive form of hydrogen very easily reacts with coal. The plots of methanol dissociation equilibria are shown in FIG. 2. It can be seen that at 10 atm. and 200° C. more than 80 percent of methanol dissociates. At 300° C. and above, almost all of the methanol is dissociated. The decomposition of methanol occurs inside the coal pores, i.e., a highly reactive form of hydrogen is produced within coal pores at the reaction site, in other words the surface area for the hydrogenation reaction is tremendously increased. Methanol is not absorbed by ash or sulfur compounds such as $CaSO_4$, $FeSO_4$, etc. so it is no decomposed in the portion of ash or pyrites or sulfates of the coal seam, and highly reactive nascent hydrogen is not produced at these sites, so there is less chance of reaction with these compounds. Thus the product is lower in sulfur content. Methanol also provides a chemical comminution (chemical fracturing of coal) effect.

The experimental evidence suggests that methanol weakens the structure and breaks the coal, and at higher temperatures and at the dissociation stage, the effect is more pronounced as the dissociation of one mole of methanol provides a total of three mole of products (1 mole of CO and 2 moles of $H_2$). This increases the local pressure in the structure of coal, and enhances the fracturing of coal. Thus, methanol increases the porosity of coal and develops permeable paths in coal for CO and $H_2$ produced by other reactions.

As methanol is absorbed by coal and not by ash and sulfur compounds, it will break coal into small particles, whereas ash and sulfates will be larger in size. The bigger particles of ash, pyrites and sulfates have lower probability of being carried over with product gases.

The temperature zones and major reactions taking place in these zones in the coal seam are shown in FIG. 3. Methanol decomposition provides carbon monoxide and nascent hydrogen which being highly reactive requires lower temperatures and pressures for gasification reactions. The nascent hydrogen produced inside the coal pores at favorable condition easily reacts with carbon in the coal to produce methane by the reaction:

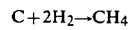

which is an exothermic reaction, and increases the temperature and provides the heat for endothermic reactions. The CO produced by decomposition of the methanol reacts with the moisture of the coal by co-shift reaction to produce additional hydrogen for hydrogasification reactions.

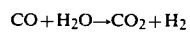

This reaction being exothermic increases the temperature and provides heat for the endothermic reactions.

Following injection, vaporization and dissociation of methanol, steam is next introduced in the coal seam in the high temperature zones. The steam reacts with carbon in the coal

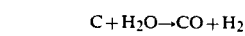

to produce CO and $H_2$. This reaction being endothermic requires heat which is supplied by the exothermic reactions taking place. The CO and $H_2$ produced provide reactants for the co-shift and methanation reactions, which are exothermic reactions which produce heat for steam carbon reaction which is endothermic. Ideally 3 moles of methanol, 38 moles of carbon and 37 moles of steam are reacted to produce 21 moles of methane and the reactions are sustained without external heat supply (refer to Table 1). Thus, a supply of heat is required only to initiate the reactions by increasing the temperature of the seam in the beginning.

The product gases contain higher methane content because of the highly reactive form of hydrogen produced at the reaction site, and the methanation reactions and co-shift reactions are favored at the lower temperatures of the present invention.

The product gases are extracted through production wells and are subjected to well developed unit operations such as gas clean up, acid-gas removal and methanol synthesis. In methanol synthesis CO and $H_2$ produced during in situ gasification can be converted to methanol by the reaction $$CO + 2H_2 \rightarrow CH_3OH$$

using commercial processes. After methanol synthesis, methanol can be condensed in the condensor. Part of the crude methanol can be recycled for injection in the coal seam and part of methanol can be sold as product after purification. The gases coming out of condensor contain mainly $CH_4$ and some CO and $H_2$ (about 700 Btu/SCF). These gases can be used as high Btu product gases or can be subjected to methanation to obtain pipeline quality gas ($\simeq$ 1000 Btu/SCF) as product.

If necessary, prior to injection of methanol, bore holes can be drilled and permeable paths developed in the coal seam. The state of the art for seam preparation is well known. There are several ways to develop permeable paths in a seam. In the present process, this is done by chemical/explosive fracturing of coal using slurry explosives such as ammoniumnitrate/aluminum/-diesel oil mixture or Du Pont EL-836. The efficiency of the explosives depends on the powder factor of the explosives. For example, 1 lb. to 2.5 lb. of Du Pont EL-836 is required to fracture 1 ton of coal at about 1000 ft. depth. In suitable deposits several thousand tons of coal can be fractured at one time to provide permeable paths within the coal seam.

Additional access holes can be drilled to the shattered region of the seam, to inject reactants from inlet holes and to recover products from the outlet holes. The process flow diagram is shown in FIG. 1.

TABLE: 1

Heat Balance for Ideal Case
Basis: 3 moles of methanol

| Favorable Temperatures* | Major Reactions | Heat of Reaction |
|---|---|---|
| Above 200° C. | $3CH_3OH \rightarrow 3CO + 6H_2$ | + 36 Kcal |
| Less than 650° C. | $3C + 6H_2 \rightarrow 3CH_4$ | − 60 Kcal |
| Less than 805° C. | $3CO + 3H_2O \rightarrow 3CO_2 + 3H_2$ | − 27 Kcal |
| Above 677° C. | $17C + 17H_2O \rightarrow 17CO + 17H_2$ | +544 Kcal |
| Less than 805° C. | $17CO + 17H_2O \rightarrow 17CO_2 + 17H_2$ | −153 Kcal |
| Less than 650° C. | $18C + 36H_2 \rightarrow 18CH_4$ | −360 Kcal |
| Overall Reaction | $3CH_3OH + 38C + 37H_2O \rightarrow 21CH_4 + 20CO_2 + H_2$ | |

Heat required for endothermic reactions = 36 + 544 = 580 Kcals
Heat supplied by exothermic reactions = −360 −153 −27 −60 = −600 Kcals

*Heat required to increase the temperature to initiate reactions and for the heat losses can be supplied by supplying oxygen to initiate the process. Also note that major reactions and favorable temperatures correspond to the temperature zones of the seam where they occur.

I claim:

1. A process for in situ gasification of coal to produce a combustible methane rich product gas which comprises injecting a lower aliphatic alcohol into an underground coal seam, raising the temperature of the seam sufficiently to cause vaporization and dissociation of the alcohol into carbon monoxide and nascent hydrogen and initiate a hydrogasification reaction, within the coal seam, and injecting water into the seam to react with the coal to form additional carbon monoxide and hydrogen which participate in said hydrogasification reaction to produce said product gas.

2. The process of claim 1 wherein said coal seam is fractured prior to said injection of methanol.

3. The process of claim 1 wherein said water is in the form of steam.

4. The process of claim 1 wherein oxygen is also injected initially into said seam.

5. The process of claim 1 wherein the temperature inside the seam subsequent to injection of said alcohol is raised by initiating by igniting the upper portion of the seam.

6. The process of claim 1 wherein the temperature in the coal seam is increased to a range of about 250° C. at the bottom of the seam to about 800° C. at the top.

7. The process of claim 1 wherein said methane rich product gas additionally contains carbon monoxide and hydrogen.

8. The process of claim 7 wherein said carbon monoxide and hydrogen contained in said product gas are separated from the methane in said gas and converted to methanol.

9. The process of claim 7 wherein a portion of said methanol is returned to the coal seam for further production of methane rich product gas.

10. The process of claim 1 wherein said alcohol is methanol or ethanol.

* * * * *